(12) United States Patent
Yi et al.

(10) Patent No.: US 9,278,696 B2
(45) Date of Patent: Mar. 8, 2016

(54) VEHICLE ONBOARD SAFETY SYSTEM

(71) Applicants: Ge Yi, San Ramon, CA (US); Dujiang Wan, Fremont, CA (US)

(72) Inventors: Ge Yi, San Ramon, CA (US); Dujiang Wan, Fremont, CA (US)

( * ) Notice: Subject to any disclaimer, the term of this patent is extended or adjusted under 35 U.S.C. 154(b) by 18 days.

(21) Appl. No.: 14/304,913

(22) Filed: Jun. 14, 2014

(65) Prior Publication Data

US 2015/0360696 A1  Dec. 17, 2015

(51) Int. Cl.
| | |
|---|---|
| *G08B 23/00* | (2006.01) |
| *B60W 40/08* | (2012.01) |
| *A61B 5/18* | (2006.01) |
| *B60K 28/06* | (2006.01) |

(52) U.S. Cl.
CPC .............. *B60W 40/08* (2013.01); *A61B 5/18* (2013.01); *B60K 28/06* (2013.01); *B60K 28/063* (2013.01); *B60W 2040/0836* (2013.01)

(58) Field of Classification Search
CPC ......... A61B 5/18; B60K 28/063; B60K 28/06
USPC ................... 340/576, 575; 180/272
See application file for complete search history.

(56) References Cited

U.S. PATENT DOCUMENTS

| | | | | |
|---|---|---|---|---|
| 4,996,161 A | * | 2/1991 | Conners | G01N 33/4972 180/272 |
| 7,330,124 B2 | * | 2/2008 | Ota | G06K 9/2036 340/576 |
| 7,616,123 B2 | * | 11/2009 | Ridder | A61B 5/0059 340/576 |
| 7,823,681 B2 | * | 11/2010 | Crespo | B60K 28/063 180/272 |
| 8,063,786 B2 | * | 11/2011 | Manotas, Jr. | A61B 5/18 340/576 |
| 8,698,639 B2 | * | 4/2014 | Fung | B60K 28/06 340/576 |
| 8,795,187 B2 | * | 8/2014 | Morley | B60K 28/063 180/272 |
| 8,874,162 B2 | * | 10/2014 | Schrader | H04M 1/72577 340/670 |

* cited by examiner

*Primary Examiner* — John A Tweel, Jr.

(57) ABSTRACT

Vehicle onboard safety systems against deception during driving-under-influence (DUI) test, using cheiloscopy sensor or bite mark sensor as biometrics have been invented. The systems have an engine interlock system, which controls the engine ignition based on the onboard DUI testing result. The systems also have a smart phone locker designed to take the smart phone away from the driver in order to avoid any driving distraction, while allowing connection to external network and resource through tethering.

18 Claims, 10 Drawing Sheets

VEHICLE ONBOARD SAFETY SYSTEM

FIELD OF INVENTION

The invention is related to a vehicle onboard safety system, which cannot be deceived. Particularly, the undeceivable system is used against driving under the influence (DUI), texting-while-driving and fatigue driving as well as unauthorized driving,

BACKGROUND ART

Major causes of fatal traffic accidents are driving under influence (DUI) and texting-while-driving, as well as fatigue driving. This is particularly true for a young driver. In fact, texting-while-driving is the number one cause of teen driver deaths.

Driving with blood alcohol content (BAC) above a limit is illegal and could cause a deadly consequence. On the other hand, widely available and accessible headache and pain relief non-prescription medicines, such as Tylenol, as well as sleeping pill can also have big influence on safe driving with potential lethal consequence.

Recent legalization of recreational marijuana in Washington could eventually lead to spread across the States. Apart from alcohol and non-prescription medicines, marijuana will be another major concern on safe driving; particularly on young drivers' safe driving. How to ensure this trend does not compromise the safe driving is one of the biggest challenges facing the U.S. Department of Transportation.

For safety's sake, it is critical and powerful to develop an undeceivable technology and system against driving under the influence of any psychoactive (mind-altering) substance and/or metal fatigue condition before and during driving.

One of the methods against driving under the influence of any psychoactive (mind-altering) substance and/or metal fatigue condition before engine start, is vehicle ignition interlock system. There are ignition interlock systems against illegal alcohol on the market already. However, existing systems are easily deceived by third party who is not under the influence of alcohol or drug. As such, none of the existing systems has turned into a main stream product despite of its relative low cost.

Two classes of undeceived vehicle onboard safety systems with ignition interlock against driving under the influence of any psychoactive (mind-altering) substance and/or metal fatigue condition, which are capable of reduction of driver's distraction during driving as well, are disclosed in this invention. These systems are particularly powerful and useful to keep teen drivers and younger drivers from driving under the influence of any psychoactive (mind-altering) substance and/or mental fatigue (MF) condition.

As used herein, the term "or" may be construed in either an inclusive or exclusive sense. Similarly, the term "exemplary" is construed merely to mean an example of something or an exemplar and not necessarily a preferred or ideal means of accomplishing a goal. Additionally, although various exemplary embodiments discussed below focus on quality control of professionals, the embodiments are given merely for clarity and disclosure. Alternative embodiments may employ other systems and methods and are considered as being within the scope of the present invention.

The following numerous specific detail descriptions are set forth to provide a thorough understanding of various embodiment of the present disclosure. It will be apparent to one skilled in the art, however, that these specific details need not be employed to practice various embodiments of the present disclosure. In other instances, well known components or methods have not been described.

SUMMARY OF THE INVENTION

In this invention, two classes of undeceived vehicle onboard safety systems with ignition interlock function are disclosed: 1) system with pre-stored drivers' information (hereafter as "SDI system"), particularly personal identity such as authorized drivers' biometrics; 2) no pre-loaded drivers' information system (hereafter as NDI system). The SDI system is suitable to be used on family or private owned vehicle while NDI system is targeted for being used on shared vehicle such as rental, leased and company-owned ones.

The SDI system has pre-stored authorized drivers' identity biometrics such as bio-identity finger prints and voice patterns. It is also capable of memorizing assigned individual driver's "user level" by super drivers (or users) such as the parents on a system installed on a family car. The system has its innovative uniqueness of design principle against deception—gathering the driver's biometrics and checking the driver's capability of safe driving, such as DUI testing, are carried out on a purposely designed device at the same time or within a time gap too short to cheat. To achieve above design principle on hardware level, in SDI system, biometrics collecting device is coupled directly with DUI testing unit. After passing identity verification and safe-driving capability test, the system grants a matching "user level" to the driver before engine starts. The engine will be interlocked if the driver fails either of them.

The NDI system uses multiple sensors instead of pre-stored driver's identity to enroll driver's characteristic such as weight, and testing the driver's capability of safe driving before engine ignition. The sensors of the system are purposely designed against deception, to ensure that the driver who sits on the driving seat and passes the test, is the one driving the vehicle after engine ignition. The driver has to pass DUI testing before engine ignition. The engine will be interlocked if the driver fails the testing.

Both SDI and NDI systems include a smartphone (and/or other mobile device) dock station or locker, which enables the system to connect to a third party network via tethering through the phone and/or the device. Between the system and the phone/the device, either wired connection or wireless near field communication systems can be used. Submitting/locking the driver's smartphone or any other mobile devices onboard becomes essential for initiating the system.

By recognizing the driver's voice pattern, the near field communication system has built-in software to provide driver voice-input texting function if allowed, and automatically disable mobile device's texting function and other apps such as video and game, etc., while vehicle engine is running, which is detected by the built-in accelerator or other sensors.

Both systems continuously check and monitor the driver's presence and driving behaviors by add-on sensors, such as infrared sensor to detect mental fatigue (MF) driving by sensing driver's head movement during driving, driver's continuous presence sensor installed on driver's seat to detect if driver swap happens after passing DUI testing, etc., to prevent safe driving from cheating and distractions. In another example, the oxygen level in driver's blood is monitored by an oximetry sensor on steering wheel.

Several testing technologies and hardware solutions are proposed in SDI system, including breath analyzer (breathometer) coupled with cheiloscopy (lip print) using technology similar to finger print sensor; breath analyzer coupled with bite-mark analysis using pressure sensor; breath analyzer coupled with facial pattern recognition or iris recognition; digitalized saliva analyzer (salivameter) coupled with cheiloscopy; digitalized saliva analyzer coupled with facial pattern recognition or Iris recognition.

For SDI system, the pre-stored driver's biometrics information can be used as a vehicle anti-theft mechanism and protective mechanism against unauthorized vehicle driving.

The NDI system comprises at least a DUI testing unit, such as alcohol (or drug, or both) testing device, fixed with an infrared emitter, which is coupled with an infrared detector in front of the driving seat for position detection of the testing unit; one infrared camera obtains the driver's thermal facial imaging without recording the facial photo picture to continuously check the driver's presence, and protect driver's privacy as well; a center control unit (CCU) with pre-loaded firmware and software for data processing and system control; an engine interlock system controlled by CCU. The system is tracking the relative position between the testing unit and the person who is under test to ensure the testing is indeed carried by the driver before engine start to defeat any cheating. The system, based on testing result, either grants or rejects driving authorization.

The NDI system has great privacy protection since the driver's characteristic information will be permanently deleted from the system as soon as the engine stops, thus cannot be used as a anti-theft device. This system is particularly useful for implementation on share vehicles such as rental or taxi vehicle with multiple drivers.

DETAILED DESCRIPTION

The following description is provided in the context of particular designs, applications and the details, to enable any person skilled in the art to make and use the invention. However, for those skilled in the art, it is apparent that various modifications to the embodiments shown can be practiced with the generic principles defined here, and without departing the spirit and scope of this invention. Thus, the present invention is not intended to be limited to the embodiments shown, but is to be accorded the widest scope consistent with the principles, features and teachings disclosed here.

Figure 1A:
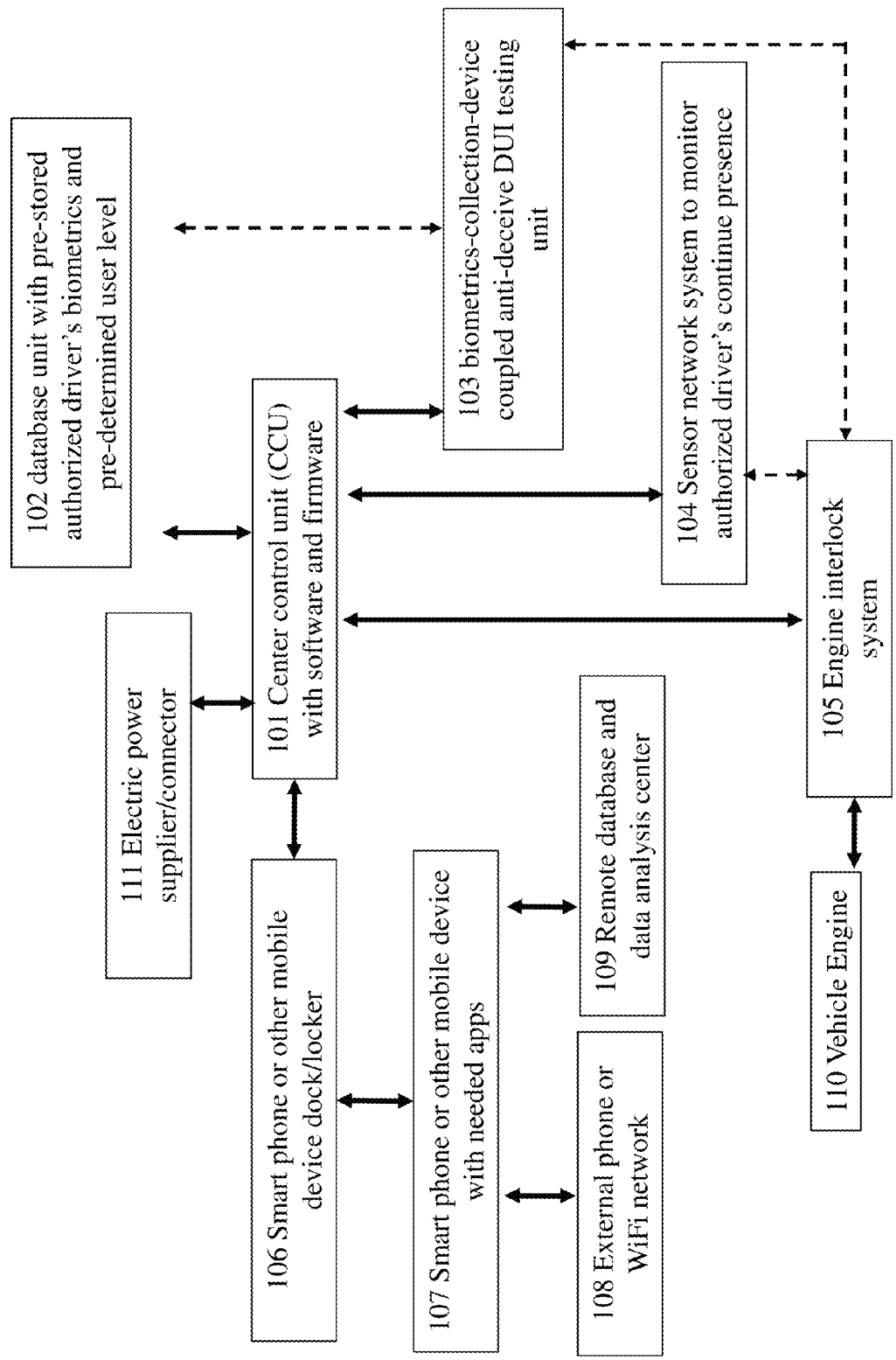
FIG. 1A Schematic diagram illustrating key components for one of embodiments of proposed SDI system.

FIG. 1A shows a system diagram illustrating key components for one of embodiments of proposed SDI system. The system comprises, at least, a center control unit (CCU) 101, with pre-loaded firmware and software, for data processing and system control; a database unit 102 with pre-stored authorized driver's biometrics and pre-determined user level; an biometrics-collection-device coupled anti-deceive driving under influence (DUI) testing unit 103; sensor network system 104 to monitor authorized driver's continuous presence; an engine interlock system 105; a smartphone or other mobile device dock/locker 106, which links to the CCU 101 and communicates through either wired or a built-in near field communication system with the submitted driver's smartphone or other mobile device; and electric power supplier (battery) or power connector 111 for a vehicle onboard safety system. The CCU 101 accesses the external phone or WiFi network 108 and remote database and data analysis center 109 by channeling through the driver's smartphone or other mobile device 107 via the dock/lock 106.

Figure 1B:
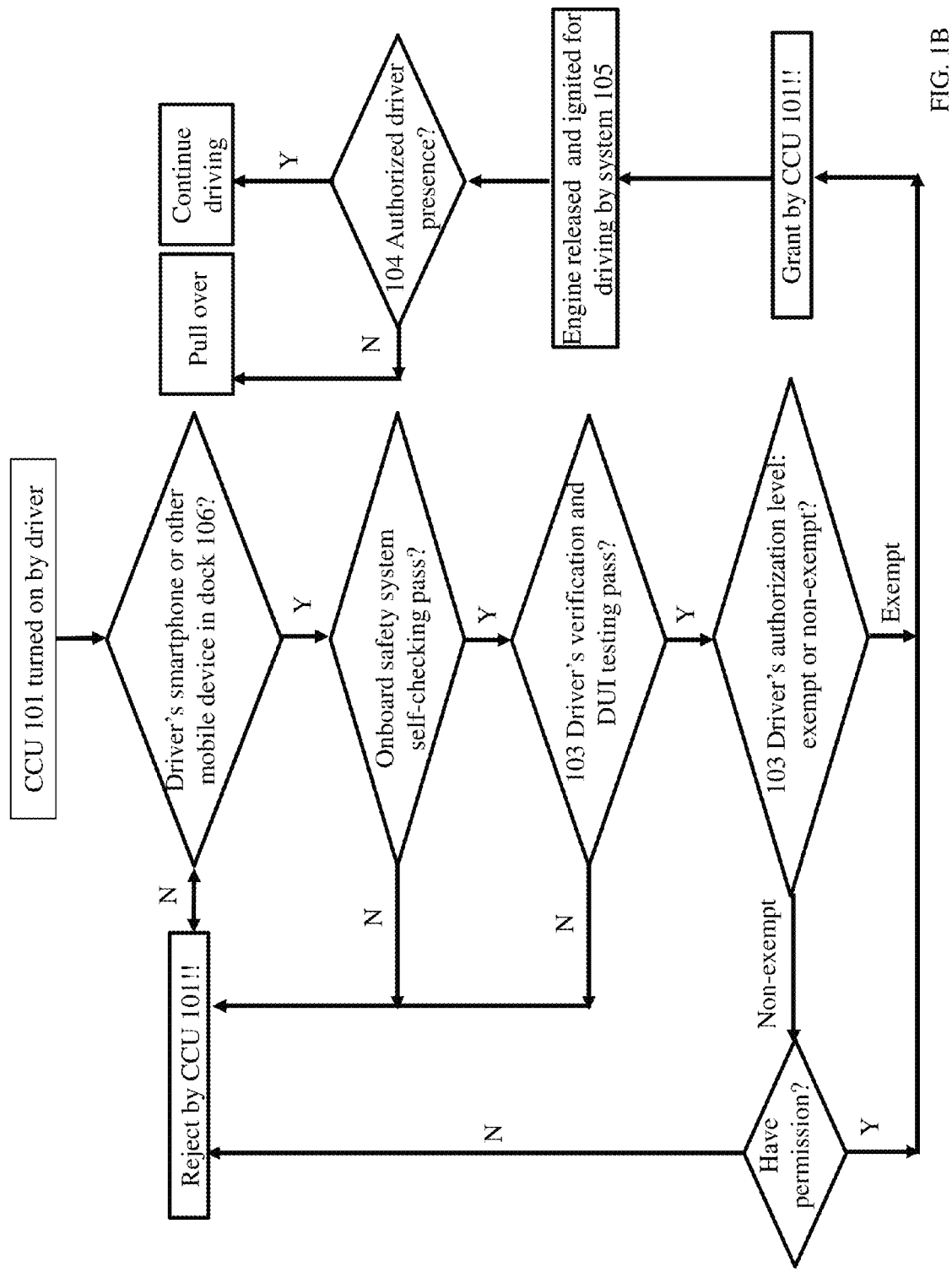
FIG. 1B Diagram illustrating how SDI system works.

For a vehicle with an installed proposed onboard safety system shown in FIG. 1A, the system will work following the decision flow chart (or decision procedure) shown in FIG. 1B.

Once the driver does the normal engine start, he or she literally turns on CCU 101 powered by electric power supplier (battery) or connector 111. CCU 101 will first ask the driver to submit his/her smartphone or other mobile device 107 into dock/locker 106, and check all the system components shown in FIG. 1A to ensure all of them working properly. CCU 101 will reject driving request and notify the pre-stored vehicle owner (and/or super users) by phone if the system self-checking fails.

After system self-checking passed, CCU 101 will start driver's identity verification, authorization level check, and DUI testing process. The identities and authorization levels of permission exempt (eg. family members) and permission non-exempt drivers (e.g. member visitors or teen drivers in the family) are pre-stored in database 102.

Firstly, the system collects the driver's biometric identity as well as DUI test result at almost the same time, from unit 103. Then it verifies the identity with the pre-stored one obtained from local database system 102 or remote database 109 which has better security protection for driver's privacy. Afterwards, the result of DUI test is checked. CCU 101 will reject driving request and notify the pre-stored vehicle owner by phone if either the driver's identity verification or DUI test fails.

Once the system verifies he or she is an authorized exempt driver based on the driver's identity, and the result from DUI test is fine, CCU 101 will grant the driver driving privilege as well as notify the pre-stored vehicle owner by phone if this option is pre-enabled during initial system configuration, and the engine interlock system 105 will release the interlock and automatically ignite the engine for driving.

For permission non-exempt driver, apart from having the same procedures as the permission exempt driver to take diver's identity verification and DUI test, the CCU 101 will contact the pre-stored vehicle owner by phone for driving permission. Once the driving permission confirmed by the vehicle owner (such as a remote code input), CCU 101 will grant the driver driving privilege, and the engine interlock system 105 will release the interlock and automatically ignite the engine for driving.

During the driving, sensor network system 104 will continuously monitor the driver's continued presence to prevent post engine start driver swap and collect the driver's driving behavior data for individual driving habit database buildup. Once driver swap is detected, both CCU 101 and engine interlock system 105 will work together to pull the vehicle over.

For the sake of safety, both CCU 101 and engine interlock system 105 will work together to control the vehicle's speed below the predetermine speed limit, particularly for driver with lower user-level (such as teen driver in the family) for their safety.

The software on CCU 101 is designed to disable certain functions of smartphone 107, which could cause driver distraction during driving, such as texting and video related apps, while tethering through the smartphone 107 to outside network 108 at emergency. The software has the function to recognize the driver's voice pattern, as well as accent, after initial training and provide driver voice-input texting through the dock/locker 106 for driver with higher user-level while, for teen driver at lower user-level, the voice-input texting can be disabled for safety concerns by super user.

Apart from the navigation and accelerator data from smartphone 107, the setup of CCU 101 prohibits other data or apps into CCU 101 to avoid hacking or virus contamination through smartphone 107. The system can also have display and speakers with or without amplifier for displaying navigation information and playing music from smartphone 107.

As mentioned previously, the system shown in FIG. 1A requests pre-loaded private data such as biometrics and phone numbers either locally or remotely. This approach provides the system as an anti-theft system. User level/tier management system with "administrator" vehicle owner can be easily implemented and integrated into this approach to restrict a family's teen or young drivers' behave during driving to protect their safety. It can even set up time slot control remotely in this system to protect youngsters' safety when they are not mature enough to have a proper self-control and time management such as late party etc.

Figure 2A:
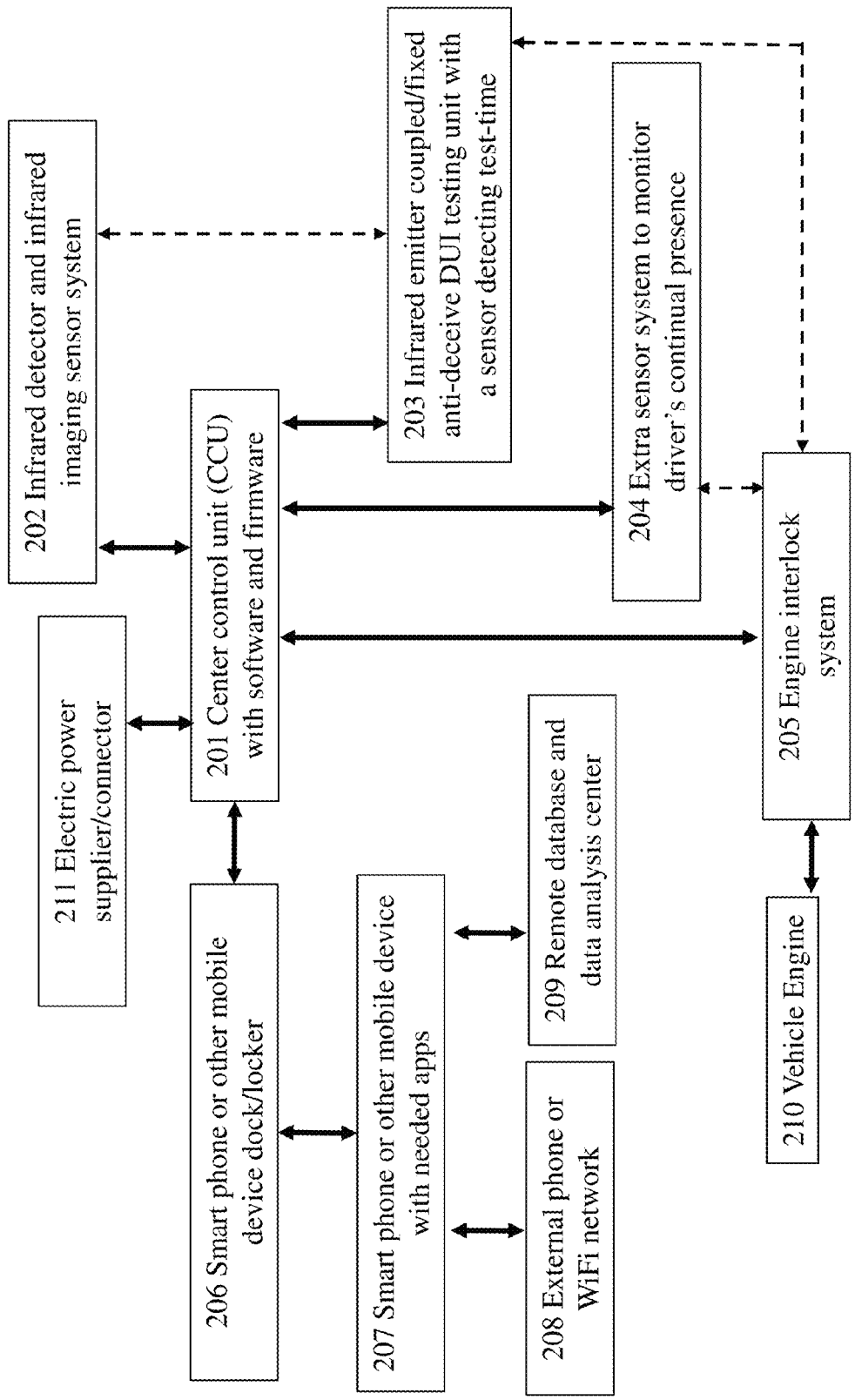
FIG. 2A Schematic diagram illustrating key components for one of embodiments of proposed NDI system.

FIG. 2A shows NDI system against deceive without the need for privacy data pre-stored on the system. This system is particularly useful for implementation on shared vehicles such as rental car or taxi car with multiple drivers.

As shown in FIG. 2A, the system comprises a center control unit (CCU) 201 with software and firmware; an infrared detector and infrared imaging sensor system 202; an infrared emitter coupled anti-deceive driver-under influence (DUI) testing unit with a sensor 203 (the infra-red emitter is permanently fixed on DUI unit while the sensor detects the exact time when testing happens); an extra sensor system 204 to monitor the driver's continuous presence; an engine interlock system 205; a smartphone or other mobile device dock/locker 206, which links to the CCU 201 and communicates through either a wired or a built-in near field communication system with the driver's smartphone or other mobile device; and electric power supplier (battery)/power connector 211 for a vehicle onboard safety system. The CCU 201 accesses the external phone or WiFi network 208 and remote database and data analysis center 209 by channeling through the driver's smartphone or other mobile device 207 via 206. The infrared detector in system 202 is pairing with the infrared emitter on the testing unit 203.

Figure 2B:
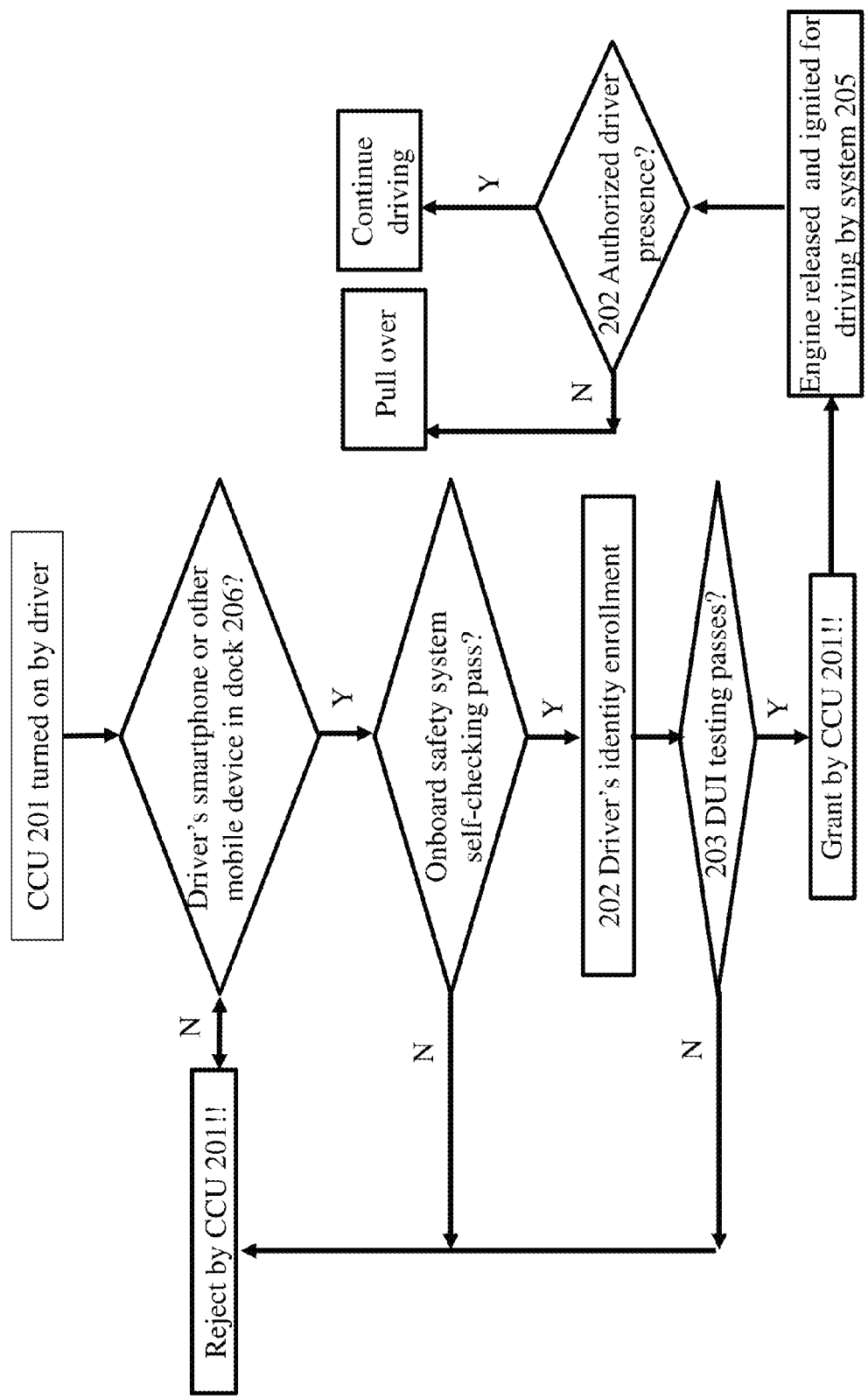
FIG. 2B Diagram illustrating how NDI system works.

For a vehicle with an installed NDI system shown in FIG. 2A, the system follows the decision flow chart (or decision procedure) as shown in FIG. 2B.

Once the driver does the normal engine start, he or she actually turns on CCU 201 powered by electric power supplier (with battery)/power connector 211. CCU 201 will first ask the driver to submit his/her smartphone or other mobile device 207 into dock/locker 206, and check all the system components shown in FIG. 2A to ensure all of them working properly. CCU 201 will reject driving request if the system self-checking fails.

After system self-checking passed, CCU 201 will start driver's characteristic data gathering (such as weight) and monitoring by infrared imaging sensor system 202 and extra sensor system 204, followed by DUI testing process by infrared emitter coupled anti-deceive DUI testing unit 203. The driver's infrared image taken by system 202 with his or her weight obtained by extra sensor system 204 will be temporarily saved in CCU 201 as the driver's characteristic data, which will be permanently deleted later after driving finishes and engine stops. The driver's characteristic data collection is named hereafter as driver's enrollment for NDI system. At the same time, the driver takes the DUI test. CCU 201 will reject driving request if the driver's DUI test fails. Once the driver's enrollment finishes and the driver passes DUI test, CCU 201 will grant the driver driving privilege and, the engine interlock system 205 will release the interlock and automatically ignite the engine for driving.

One way, the NDI system defeats cheating by continually tracking the infrared emitter coupled DUI testing unit by 202, which also constantly takes the infrared facial image of the driver sitting on the driving seat. By checking the overlapping of the facial images and location of DUI testing unit, the NDI system ensures, during the DUI testing, the person on the driving seat is the only one, who takes the DUI test.

The other way, the NDI system, against deception, is designed in such a way that, whenever a person on driving seat takes the DUI testing, the sensor on DUI test unit 203 triggers an infrared signal emitting from unit 203, and will further activate the infrared detector and infrared imaging sensor system 202 by CCU 201 to record a static facial infrared image as well as location of the DUI unit via the location of the infrared emitter in CCU 201. The CCU 201 uses the image processing to ensure the DUI testing is carried out by the person on the driving seat. The person's weight data and his or her static facial infrared image in CCU 201 together form the driver's enrolled characteristic data.

During the driving, the infrared imaging sensor system 202 will monitor the authorized driver's presence by continuously taking his or her infrared images and comparing with the enrollment image to prevent post engine start driver swap. Extra sensor system 204 will monitor the authorized driver's continue presence too and collect the driver's driving behavior data as part of the vehicle history record, which is then used, along with the vehicle parts usage history data recorded by onboard vehicle maintenance computer, to provide the driver-vehicle system safety performance analysis in both SDI and NDI systems for vehicle maintenance and wear parts' lifetime estimation. This information is particularly useful for rental or leased car to predict next needed maintenance. Once driver swap is detected, both CCU 201 and engine interlock system 205 will work together to pull the vehicle over.

For the sake of safety, both CCU 201 and engine interlock system 205 will work together to control the vehicle's speed below the predetermine speed limit.

The CCU 201 channels through dock/locker 206 and smartphone 207 to access external network 208 as well as remote information center 209 for outside information, such as traffic and weather information, etc.

The software on CCU 201 is designed similar to the one on CCU 101 to disable certain functions of smartphone 207, which could cause driver distraction during driving, such as texting and video related apps, while tethering through the smartphone 207 to outside network 208 at emergency. The software has the function to recognize the driver's voice pattern as well as accent after initial training and provide driver voice-input texting through the dock/locker 206.

Apart from the navigation and accelerator data from smartphone 207, the setup of CCU 201 prohibits data or apps from smartphone 207 into the CCU 201 to avoid hacking or virus contamination through smartphone 207. The system can also have display and speakers with or without amplifier for displaying navigation information and playing music from smartphone 207.

Figure 3:
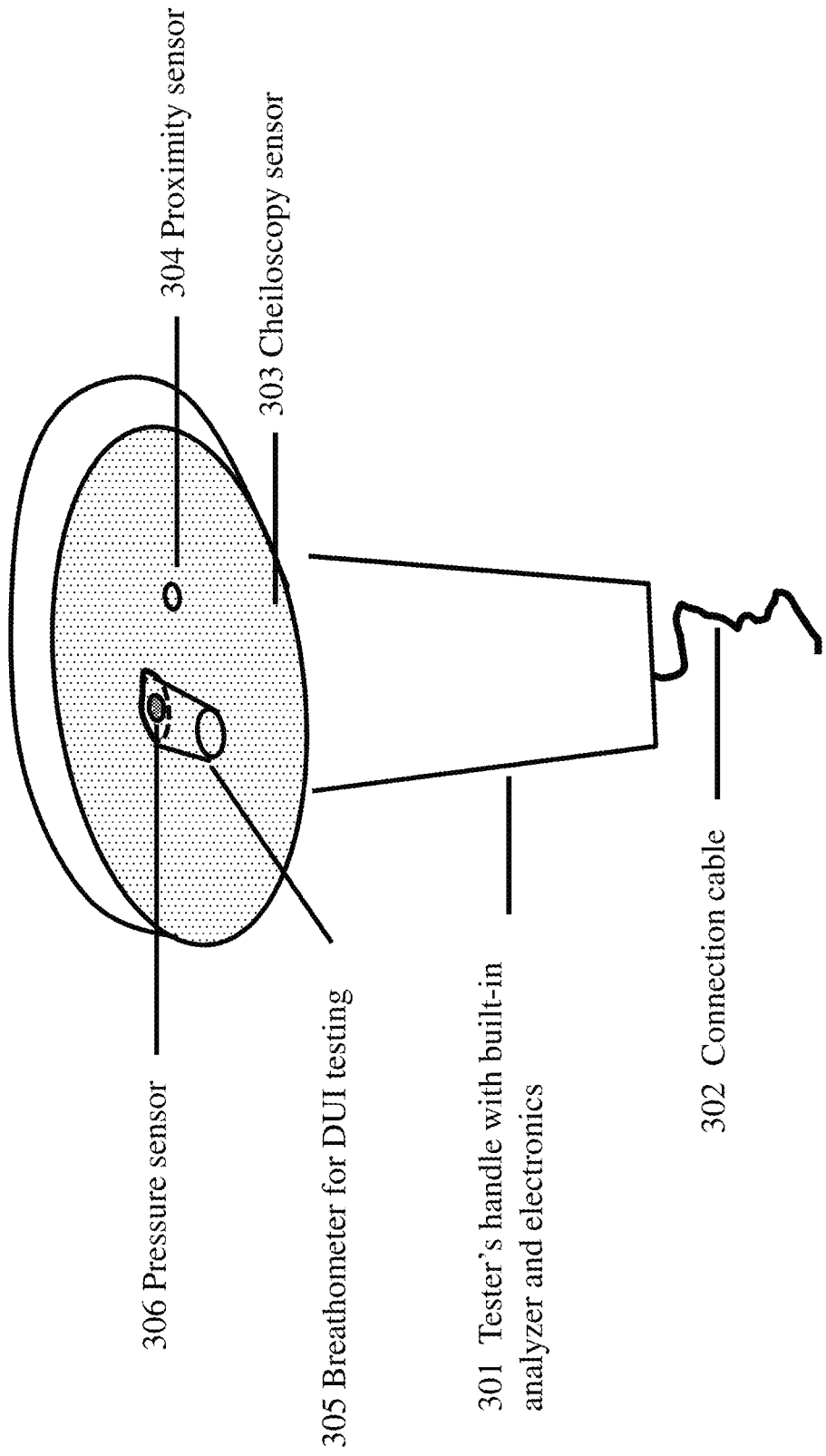
FIG. 3 A schematic for one of embodiments for the hardware solution of the testing unit 103 in FIG. 1A for SDI system—using lip print collecting sensor as biometric identity gathering device and breathometer for DUI testing.

FIG. 3 is schematic for one of embodiments for the hardware solution of the testing unit 103 in FIG. 1A for SDI system—using lip print collecting sensor as biometric identity gathering device and breathometer for DUI testing. It is well documented in literature that the lip print is a biometrics varying person-by-person. In FIG. 3, lip print is used as the driver's identity, which is collected by cheiloscopy sensor and analyzed in CCU 101 in FIG. 1A. The testing unit includes a testing handle with built-in DUI analyzer and electronics 301; connection cable 302 that links to CCU 101 in FIG. 1A; a cheiloscopy sensor 303 to collect lip print, which covers all or partial of the front of the unit; an proximity sensor 304 integrated with the cheiloscopy sensor to ensure proper lip print collection; an integrated breathometer 305 for DUI testing with a piece of consumable mouth cover; and a pressure sensor 306 in the path of the breathometer blow entry to detecting the exact time when the breath test takes place.

Following the onboard safety system self-checking in FIG. 1B, CCU 101 in FIG. 1A will start driver's DUI testing, identity verification, and authorization level check. The testing unit shown in FIG. 3 approaches to driver's mouth to start a DUI breath blow testing using the breathometer 305. The breath blow testing detected by pressure sensor 306 further triggers the cheiloscopy sensor 303 to correctly collect the driver's lip print under the help of the proximity sensor 304 for the driver's identity verification and user level determination.

Figure 4:
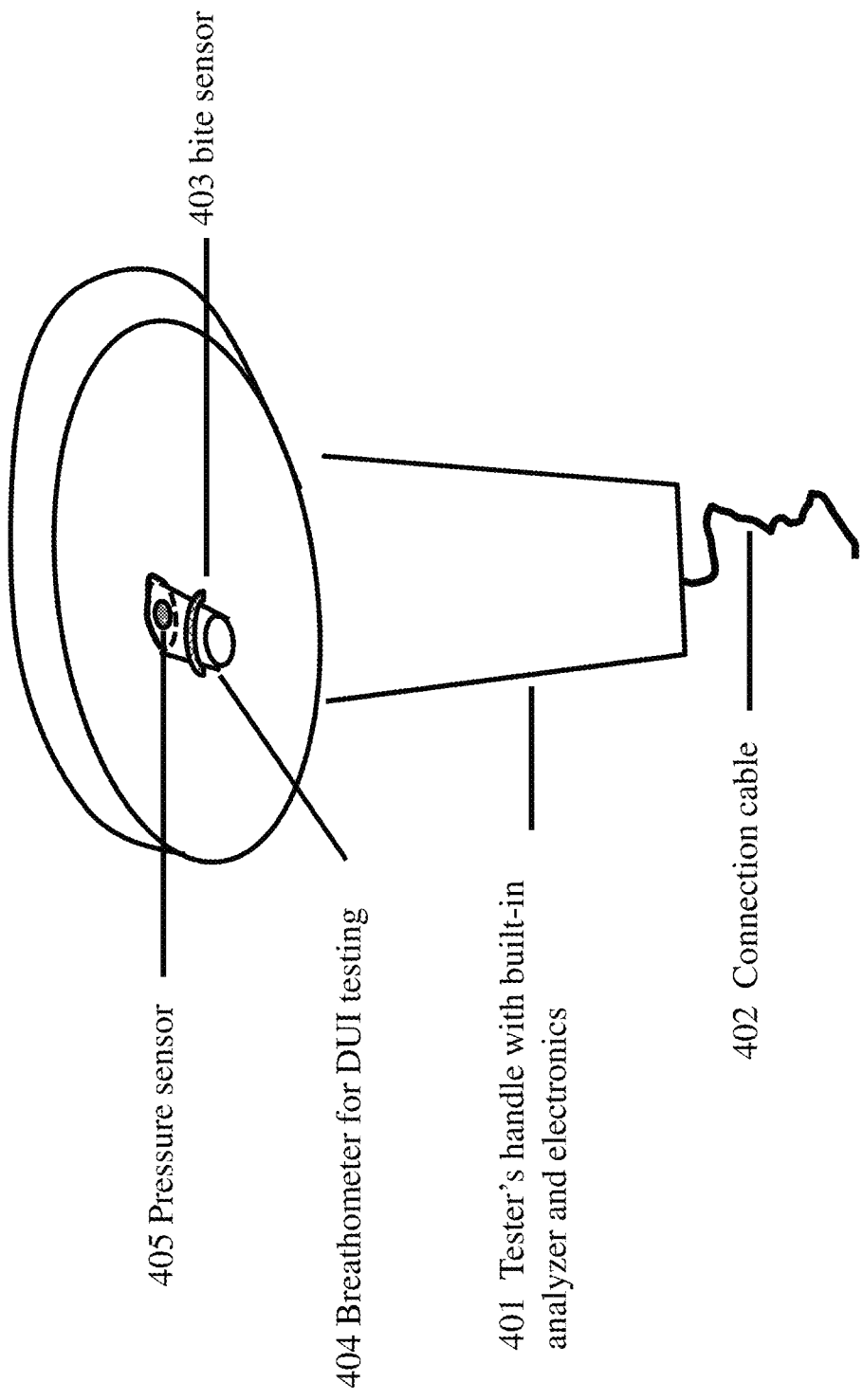
FIG. 4 A schematic for one of the embodiments for the hardware solution of the testing unit 103 in FIG. 1A for SDI system—using bite mark as biometric identity and breathometer for DUI testing.

FIG. 4 shows a schematic for one of the embodiments for the hardware solution of the testing unit 103 in FIG. 1A for SDI system—using bite mark as biometric identity and breathometer for DUI testing. Bite mark in forensic dentistry is one of methods accepted by court for personal identification. In FIG. 4, bite mark collected by a bite sensor is used as the driver's identity, which is analyzed in CCU 101 in FIG. 1A. The testing unit includes a testing handle with built-in DUI analyzer and electronics 401; connection cable 402 that links to CCU 101 in FIG. 1A; a bite sensor 403; an integrated breathometer 404 for DUI testing with a piece of consumable mouth cover; and a pressure sensor 405 in the path of the breathometer blow entry.

Following the onboard safety system self-checking in FIG. 1B, CCU 101 in FIG. 1A will start driver's DUI testing, identity verification, and authorization level check. The testing unit shown in FIG. 4 approaches to driver's mouth to start a DUI breath blow testing using the breathometer 404. The breath blow testing detected by pressure sensor 405 further triggers the bite sensor 403 to collect the driver's bite mark for the driver's identity verification and user level determination.

The time gap between bit data collection and blow testing has to be shorter than the predetermined delay time, which is too short to be cheat. The test with the time gap longer than the predetermined delay time will be disqualified by CCU 101 in FIG. 1A.

The bite sensor could be an array of capacitive pressure sensors surrounding to the breath blow testing tube.

Figure 5:
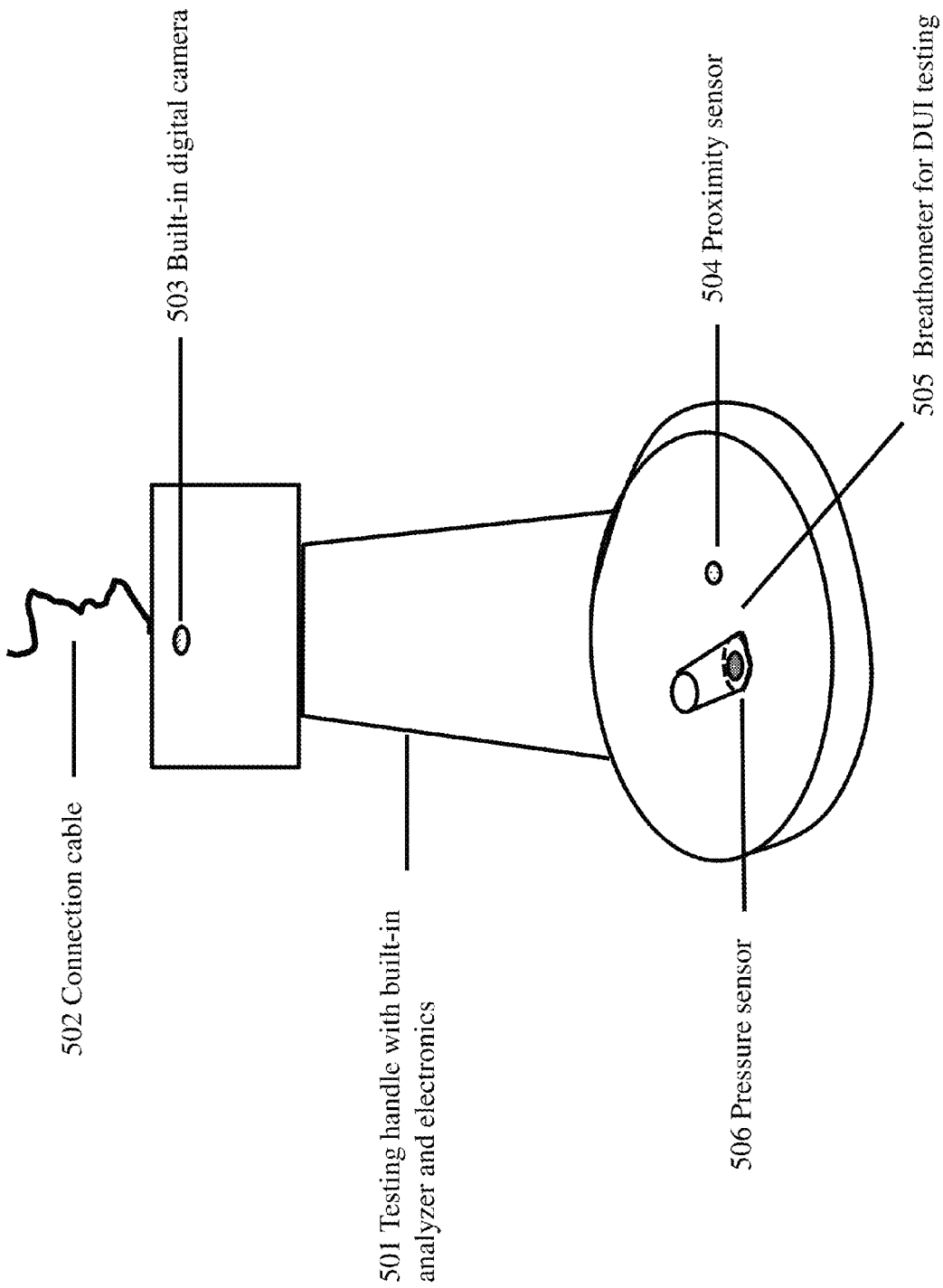
FIG. 5 A schematic for one of the embodiments for the hardware solution of the testing unit 103 in FIG. 1A for SDI system—using built-in digital camera for identity verification and breathometer for DUI testing.

FIG. 5 shows a schematic for one of the embodiments for the hardware solution of the testing unit 103 in FIG. 1A for SDI system—using built-in digital camera for identity verification and breathometer for DUI testing. The testing unit includes a testing handle with built-in DUI analyzer and electronics 501; connection cable 502 that links to CCU 101 in FIG. 1A; a built-in digital camera 503 for collecting facial or iris image; an proximity sensor 504 to ensure proper distance for image taking; an integrated breathometer 505 for DUI testing with a piece of consumable mouth cover; and a pressure sensor 506 in the path of the breathometer blow entry.

CCU 101 in FIG. 1A will start driver's DUI testing, identity verification, and authorization level check after the onboard safety system self-checking in FIG. 1B passes. The testing unit shown in FIG. 5 approaches to driver's mouth to start a DUI breath blow testing using the breathometer 505. The breath blow testing detected by pressure sensor 506 further triggers the built-in digital camera 503 to take a snap of either the driver's facial or iris image for the driver's identity verification and user level determination under the help of the proximity sensor 504.

Figure 6:
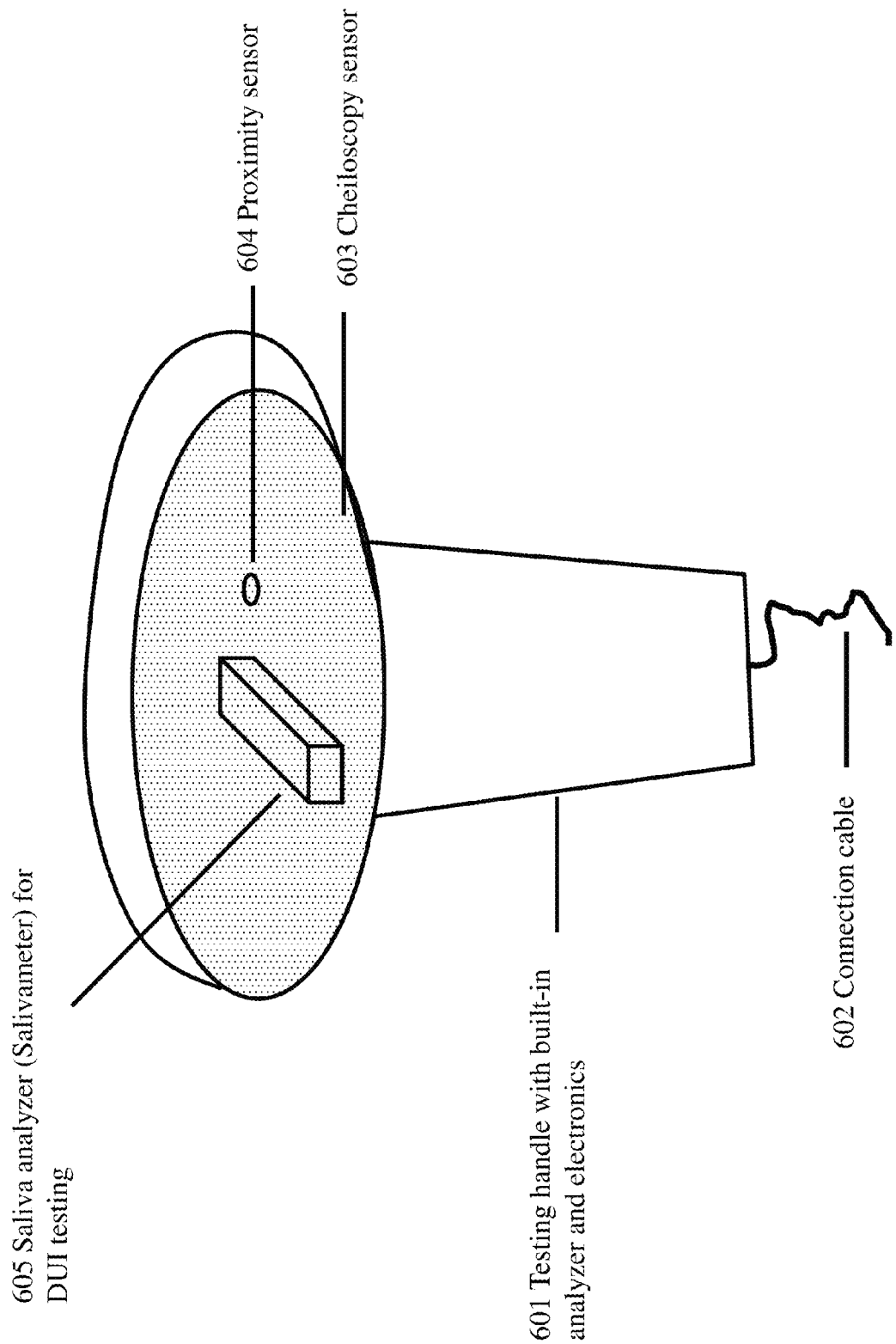
FIG. 6 A schematic for one of the embodiments for the hardware solution of the testing unit 103 in FIG. 1A for SDI system—using lip print as biometric identity and salivameter for DUI testing.

FIG. 6 shows a schematic for one of the embodiments for the hardware solution of the testing unit 103 in FIG. 1A for SDI system—using lip print as biometric identity and salivameter for DUI testing.

Saliva test is an accurate method to determine BAC (Degutis L C, Rabinovici R, Sabbaj A, Mascia R, and D'Onofrio G., *Acad Emerg Med.*, 11(8):885-7, 2004), and saliva test strip is already available on market. However, saliva strip DUI testing can be deceived by third party, and is not a good method for anti-deceive driving DUI test.

The saliva DUI test unit shown in FIG. 6 comprises a testing handle with built-in DUI analyzer and electronics 601; connection cable 602 that links to CCU 101 in FIG. 1A; a cheiloscopy sensor 603 to collect lip print, which covers all or partial of the front of the unit; an proximity sensor 604 integrated with the cheiloscopy sensor to ensure proper lip print collection; an integrated salivameter 605 for DUI testing with a piece of consumable mouth cover.

Once CCU 101 in FIG. 1A starts the procedure of driver's DUI testing, identity verification, and authorization level check, the testing unit shown in FIG. 6 approaches to driver's mouth to start a DUI saliva testing using the salivameter 605. Meanwhile, the cheiloscopy sensor 603 collects the driver's lip print under the help of the proximity sensor 604 for the driver's identity verification and user level determination. The system is designed in such a way that collecting of saliva and gathering lip print happen at the same time or within a small predetermined time gap too short to cheat.

Figure 7:
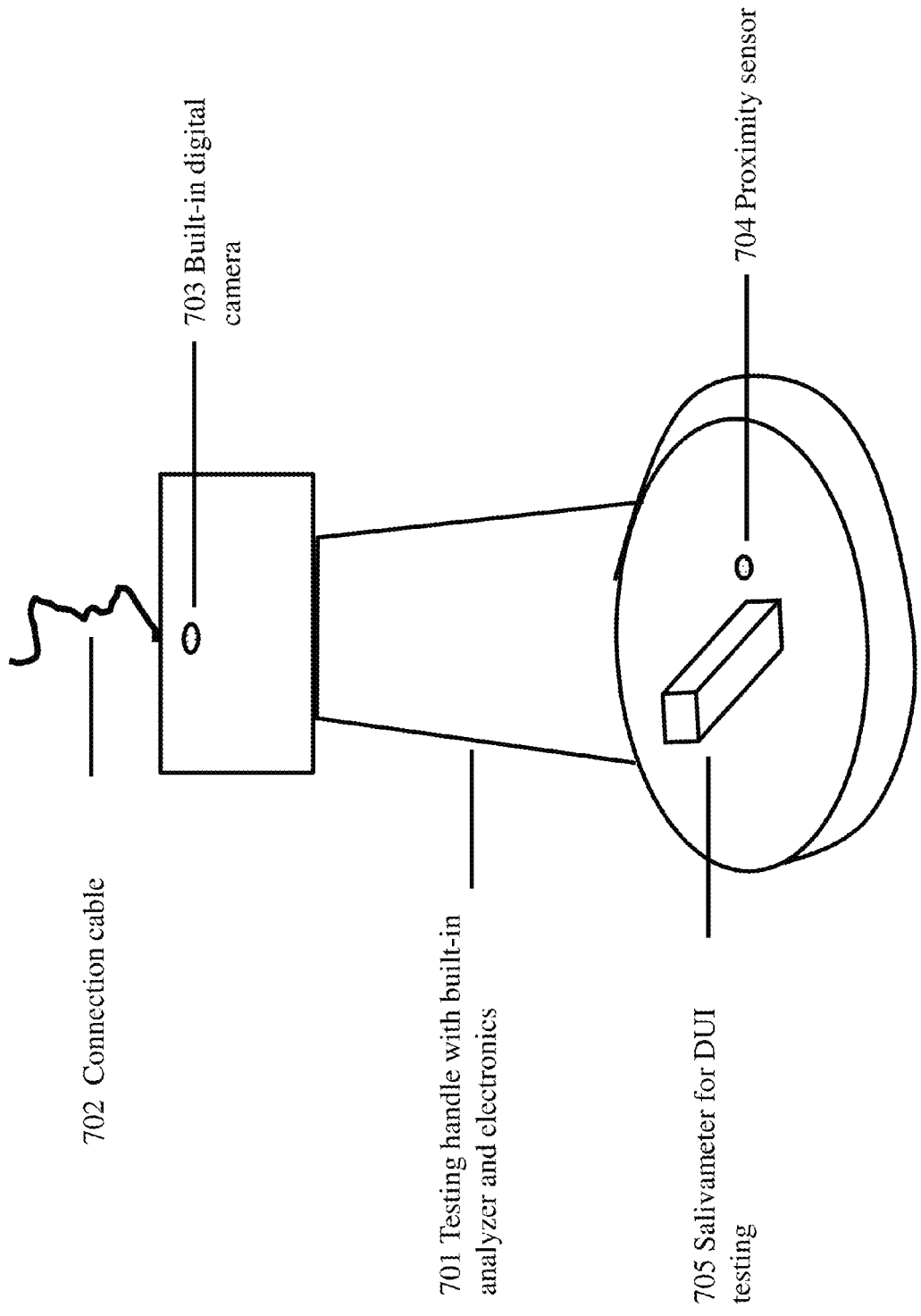
FIG. 7 A schematic for one of the embodiments for the hardware solution of the testing unit 103 in FIG. 1A for SDI system—using a built-in digital camera for identity verification and salivameter for DUI testing.

FIG. 7 shows a schematic for one of the embodiments for the hardware solution of the testing unit 103 in FIG. 1A for SDI system—using a built-in digital camera for identity verification and salivameter for DUI testing. The testing unit in FIG. 7 comprises a testing handle with built-in DUI analyzer and electronics 701; connection cable 702 that links to CCU 101 in FIG. 1A; a built-in digital camera 703 for collecting facial or iris image; an proximity sensor 704 to ensure proper distance for image taking; an integrated salivameter 705 for DUI testing with a piece of consumable mouth cover.

During the procedure of driver's DUI testing, identity verification, and authorization level check, the testing unit shown in FIG. 7 approaches to driver's mouth to start a DUI saliva testing using the salivameter 705. Meanwhile, the built-in digital camera 703 takes a snap of either the driver's facial or iris image for the driver's identity verification and authorization level check under the help of the proximity sensor 704. The system is designed in such a way that collecting of saliva and image taking happen at the same time or within a small predetermined time gap too short to cheat.

There are two proposed system configurations for the salivameter shown in both FIG. 6 and FIG. 7. The simple proposed one of the salivameter is using saliva testing paper combined with optical digital imaging sensor. The other one is using the fluorescence microarray with activation light source combined with digital imaging sensor.

Both systems employ digitized saliva test RGB images that can be processed either locally in CCU 101 or remotely at the data analysis center 109 in FIG. 1A. By comparing the digitized saliva test RGB image with threshold limit calibrated RGB image, CCU 101 in FIG. 1A determines whether the driver passes the DUI testing or not.

The designs of the salivameter will be disclosed in details in our related separated patent application.

Figure 8:
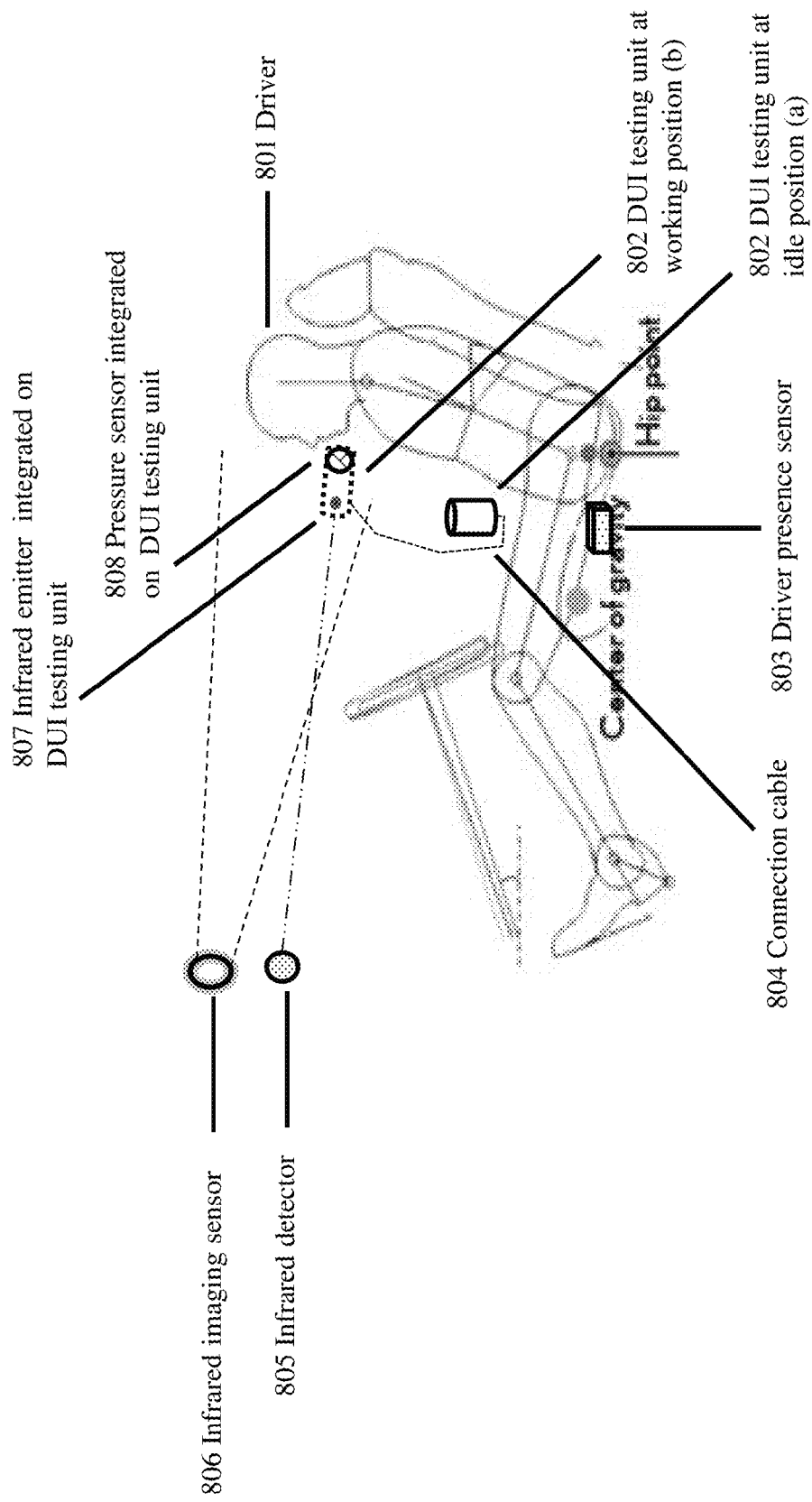
FIG. 8 A schematic of one of the embodiments of multiple-sensor-based design for the proposed NDI system shown in FIG. 2A.

FIG. 8 illustrates a schematic of one of the embodiments of multiple-sensor-based design for the proposed NDI system shown in FIG. 2A. The system comprises a DUI testing unit 802, which can be either a breathometer based unit as shown in FIG. 3, FIG. 4 and FIG. 5 or a salivameter based unit as shown in FIG. 6 and FIG. 7; a driver presence sensor 803; connection cable 804 that links to CCU 201 in FIG. 2A; a pair of infrared emitter 807 integrated on DUI testing unit 802 and infrared detector 805; an infrared imaging sensor 806 to continuously track the driver's thermal imaging around the face during DUI testing and driving. A pressure sensor 808 integrated on DUI testing unit 802 is used to control DUI testing action. The DUI testing unit can be either at idle position 802(*a*) or working position 802(*b*).

Once the sensor 803 detects a driver 801 sitting on the driver seat and the driver 801 does the normal engine start, the vehicle onboard safety system shown in FIG. 2A starts self-checking procedure. After passing self-checking procedure, the whole sensor network shown in FIG. 8 can be activated by switching the unit 802 from its idle position towards its working position for DUI testing.

When the person on driving seat takes the DUI testing, the sensor 808 on DUI testing unit 802 will trigger the infrared imaging sensor 806 to record the person's static facial infrared images. Using the data from both the infrared imaging sensor 806 and the infrared detector 805, the CCU 201 in FIG. 2A checks the fact first whether it is the person on the driver seat takes the DUI test before proceeding to check the DUI testing results.

Once the person on the driver seat passes the DUI testing, the CCU 201 in FIG. 2A will grant the driver driving privilege and, the engine interlock system 205 in FIG. 2A will release the interlock and automatically ignite the engine for driving. Otherwise, the driving request will be rejected by the CCU 201 in FIG. 2A.

The FIG. 8 only shows partial configuration of system shown in FIG. 2A to illustrate how the sensor system is arranged when it is installed on the vehicle. FIG. 8 does not give how the smartphone or other mobile device dock 206 in FIG. 2A is configured.

What is claimed is:

1. A vehicle onboard safety system comprising:
 a DUI testing unit closely coupled with a cheiloscopy sensor to collect an intended driver's lip print as biometrics while taking DUI test;
 a central control unit (CCU) to manage the system;
 a storage device with pre-stored authorized driver's or drivers' lip print biometrics and DUI limited values, which are used by said CCU to do a comparison with the data collected from said DUI testing unit;
 an engine ignition interlock system controlled by said CCU based on said comparison;
 a sensor system to ensure said intended driver, who takes and passes the test on said DUI testing unit before engine starts is the one who drives the vehicles.

2. The system of claim 1, wherein said vehicle onboard safety system further comprises a mobile device locker to hold a submitted smart phone before the vehicle engine starts.

3. The system of claim 2, wherein said vehicle onboard safety system is capable of connecting an external network through said submitted smart phone in said mobile device locker.

4. The system of claim 2, wherein said mobile device locker has a built-in software system to automatically disable mobile device's texting function to avoid driver distraction.

5. The system of claim 1, wherein said engine ignition interlock system keeps the engine at standby status before the DUI test, and further ignites the engine for driving after said comparison matches otherwise stops the engine.

6. The system of claim 1, wherein said storage device is a local device.

7. The system of claim 1, wherein said storage device is a remote data center.

8. The system of claim 1, wherein said DUI testing unit is a breathometer.

9. The system of claim 1, wherein said DUI testing unit is a salivameter.

10. The system of claim 9, wherein said salivameter is a digitalized salve analyzer, which digitizes and converts the saliva testing optical image obtained from salve testing paper under white eliminating light source to red-green-blue (RGB) numbers for automatic data analysis by comparing saliva testing results with pre-determinate threshold numbers.

11. The system of claim 1, wherein said vehicle onboard safety system further comprises a sensor network system to monitor the driver's continuous presence to prevent driver swap post engine start.

12. The system of claim 1, wherein said vehicle onboard safety system has at least a predetermined super user, who has privilege to grant a guest driver to bypass the system's biometrics confirmation but yet request for DUI test.

13. The system of claim 1, where said vehicle onboard safety system further comprise a set of sensor system to collect the driving behavior (or driving style) data of the driver as part of the vehicle history record for vehicle maintenance and wear parts' lifetime analysis and estimation.

14. A vehicle onboard safety system comprising:
 a DUI testing unit closely coupled with a bite mark sensor to collect an intended driver's bite mark as biometrics while taking DUI test;
 a central control unit (CCU) to manage the system;
 a storage device with p bred authorized driver's or drivers' bit mark biometrics and DUI limited values, which are used by said CCU to do a comparison with the data collected from said DUI testing unit;
 an engine ignition interlock system controlled by said CCU based on said comparison;

a sensor system to ensure said intended driver, who takes and passes the test on said DUI testing unit before engine starts is the one who drives the vehicles.

15. The system of claim 14, wherein said DUI testing unit is a breathometer.

16. The system of claim 14, wherein said DUI testing unit is a salivameter.

17. The system of claim 16, wherein said salivameter is a digitalized salve analyzer, which digitizes and converts the saliva testing optical image obtained from salve testing paper under white eliminating light source to red-green-blue (RGB) numbers for automatic data analysis by comparing saliva testing results with pre-determinate threshold numbers.

18. The system of claim 14, wherein said engine ignition interlock system keeps the engine at standby status before the DUI test, and further ignites the engine for driving after said comparison matches, otherwise stops the engine.

* * * * *